(12) United States Patent
Krause

(10) Patent No.: US 8,353,935 B2
(45) Date of Patent: *Jan. 15, 2013

(54) FLEXIBLE SPINE COMPONENTS HAVING A CONCENTRIC SLOT

(76) Inventor: William R. Krause, Charlottesville, VA (US)

( * ) Notice: Subject to any disclaimer, the term of this patent is extended or adjusted under 35 U.S.C. 154(b) by 604 days.

This patent is subject to a terminal disclaimer.

(21) Appl. No.: 12/497,593

(22) Filed: Jul. 3, 2009

(65) Prior Publication Data

US 2009/0270921 A1 Oct. 29, 2009

Related U.S. Application Data

(63) Continuation-in-part of application No. 12/069,934, filed on Feb. 14, 2008.

(60) Provisional application No. 61/077,892, filed on Jul. 3, 2008.

(51) Int. Cl.
*A61B 17/70* (2006.01)

(52) U.S. Cl. ....................................... 606/255

(58) Field of Classification Search .......... 606/254–259; 623/17.11–17.16
See application file for complete search history.

(56) References Cited

U.S. PATENT DOCUMENTS

| | | | | |
|---|---|---|---|---|
| 4,657,550 A * | 4/1987 | Daher | 623/17.11 |
| 5,395,370 A * | 3/1995 | Muller et al. | 606/276 |
| 5,571,192 A * | 11/1996 | Schonhoffer | 623/17.11 |
| 6,296,644 B1 * | 10/2001 | Saurat et al. | 606/256 |
| 6,986,771 B2 * | 1/2006 | Paul et al. | 606/254 |
| 7,322,982 B2 * | 1/2008 | Vincent-Prestigiacomo | 606/246 |
| 7,329,258 B2 * | 2/2008 | Studer | 606/250 |
| 7,621,940 B2 * | 11/2009 | Harms et al. | 606/257 |
| 7,717,941 B2 * | 5/2010 | Petit | 606/257 |
| 7,766,915 B2 * | 8/2010 | Jackson | 606/86 A |
| 8,043,339 B2 * | 10/2011 | Hudgins et al. | 606/255 |
| 2003/0220643 A1 * | 11/2003 | Ferree | 606/61 |
| 2005/0203517 A1 * | 9/2005 | Jahng et al. | 606/61 |
| 2007/0016204 A1 * | 1/2007 | Martinez et al. | 606/69 |

* cited by examiner

*Primary Examiner* — Alvin Stewart
*Assistant Examiner* — Jerry Cumberledge
(74) *Attorney, Agent, or Firm* — Sheldon H. Parker, Esq

(57) ABSTRACT

The invention relates to a flexible spine stabilization and/or vertebral replacement system and having one or more flexible segments within a spinal element. The flexibility is created through the use of at least one circumferential slot formed in the spinal element. One or more fasteners are connected to the distal and proximal attachments and secured to the vertebra. The spinal element can have an elastomeric material in any or all of the following combinations: filling at least one of the at least one slot; at least a portion of the inside core; encompass at least a portion of the exterior diameter. Vertebral replacement is achieved by securing the spinal element to healthy inferior and superior vertebra through use of securing members.

27 Claims, 16 Drawing Sheets

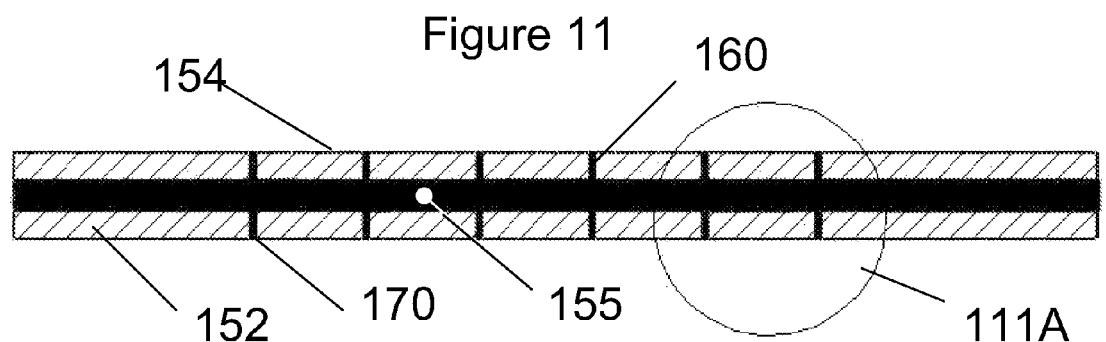
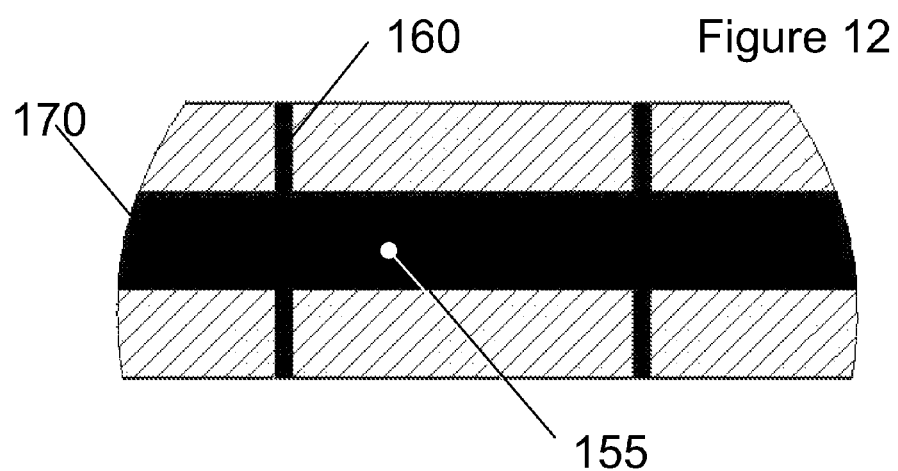

FLEXIBLE SPINE COMPONENTS HAVING A CONCENTRIC SLOT

CROSS REFERENCE TO PRIOR APPLICATIONS

This application claims priority from provisional application 61/077,892 filed Jul. 3, 2008 and is a continuation in part of pending application Ser. No. 12/069,934 filed Feb. 14, 2008, the disclosures of which are incorporated herein as though recited in full.

FIELD OF THE INVENTION

This invention relates to improved flexible elements for the incorporation in spinal implants. Specifically the invention relates to flexible rod connectors for dynamically stabilizing a portion of the spine by stabilizing two or more bone segments. Additionally, the flexible elements can be used as a vertebral body replacement implant for the replacement of one or multiple spinal vertebra which can possess, at least in one direction, the stiffness properties of the vertebra/disc combination.

BACKGROUND OF THE INVENTION

Brief Description of the Prior Art

Flexible Fixation Device

The use of fixation devices for the treatment of vertebrae deformities and injuries is well known in the art. Various fixation devices are used in medical treatment to correct curvatures and deformities, treat trauma and remedy various abnormal spinal conditions. Spinal fusion is the standard method of treatment for many conditions including spondylolysis, spinal stenosis and other disc disorders. Since fusions expanded to treat more conditions and the number of procedures is rising each year, it was apparent that many surgeons believed this procedure is the best possible treatment for their patients. Over the past decades, a variety of spinal implant devices have been used in conjunction with fusion, including rigid systems such as bone plates, intravertebral cages, rods and hooks, and pedicle screws.

Research shows that, when used properly, pedicle screws are the most reliable spinal implant, providing stabilization even in the event of pseudoarthrodesis. This posterior stabilization system involves variable-angle screws inserted into the pedicle of the vertebrae. Fluoroscopic pedicle screws can be detected by radiographic and fluoroscopic imaging during placement, improving the success rate of surgery. These rigid implants can be inserted from an anterior or a posterior approach, although the majority of physicians use the posterior technique. U.S. Pat. No. 6,645,207 to Dixon teaches a posterior system comprised of bone plates, clamps and pedicle screws that allow axial stress in order to improve the fusion procedure by placing it under pressure. Compression at the graft interface is crucial to establishing blood supply and nutrients to the graft. The '207 patent demonstrates that physiological loads and stresses are important to achieve proper healing or adjustment of a damaged vertebrae. Similar patents in this field include U.S. Pat. No. 5,437,669 to Yuan, U.S. Pat. No. 5,474,555 to Puno, and U.S. Pat. No. 6,468,276 to McKay.

There are severe limitations of the fusion procedure including unnatural stresses on the vertebrae adjacent to the fusion, extreme limitation of flexional and torsional movements, and frequent in vivo failure of rigid constructs. These problems stimulated research on dynamic stabilization devices.

Dynamic stabilization is an alternative to vertebral body fusion that stabilizes the damaged spine while permitting motion. The instruments used in dynamic fixation emanate from devices used in conjunction with fusion and are embodied in many different inventions. Pedicle screws are used with the majority of these "soft" stabilization methods, and provide physiologic support and controlled motion by attaching to elastic ligaments or metal rods. Soft stabilization devices are designed to restore the biomechanics of a functional spinal segment. Although the soft stabilizing devices relieve many problems caused by fusion, they also increase the chance of implant failure or improper insertion.

Allowing certain degrees of physiologic motion while maintaining proper rigidity to enhance healing is the most difficult aspect of the design process in the field of dynamic spinal stabilization. The Graf ligament is one of the earliest nonfusion techniques, consisting of elastic bands looped around pedicle screws. U.S. Pat. No. 5,092,866 to Breard and Graf describes this system of non-metallic loops, secured to either the spinous processes or pedicle screws, which permit the patient certain degrees of flexional and torsional movements. The semi-elastic ligament keeps sufficient space between the vertebrae which encourages proper healing. This idea has been sophisticated by subsequent researchers who have produced new methods to neutralize unstable vertebrae and the following are some typical inventions in this field. U.S. Pat. No. 6,966,910 to Ritland describes two pedicle screws anchoring a metallic rod component with several embodiments, including multiple geometries and dual rods. In the '910 device, the geometry of the metal rods produce the flexible or semi-elastic stabilization. U.S. Pat. No. 5,282,863 to Burton teaches a system that achieves dynamic fixation of the spinal column by using a non-metallic, porous material as the rod component, rather than conventional metallic rods, to increase flexibility of the implant. U.S. Pat. No. 7,083,621 to Shaolian that utilizes ball-and-socket connections between rods and bone screws that dynamically stabilize the damaged spine. The specialized rods described in the '621 patent can be inserted into the portals of the bone anchors and allow for angular articulation of the device. U.S. Pat. No. 7,018,379 to Drewry teaches a system of bone screws and fasteners that attach a flexible elongated member which is tensioned to provide corrective forces to the spine. Another motion-preserving device presented in U.S. Pat. No. 6,989,011 to Paul incorporates at least one tube with helical slits down the length. This dynamic rod or rods act to support a vertebral motion segment and allow controlled degrees of movement. The angular range of the '011 rod can be modified by altering the pitch and direction of the slits. U.S. Pat. No. 6,293,949 to Justis uses a longitudinal member at least partially composed of a pseudo-elastic shape-memory material that is anchored by bone screws. The longitudinal member reforms to a new configuration under stress then returns to the initial configuration when the stress is removed, providing flexible support for the cervical spine Subsequent researchers who have produced new methods to neutralize unstable vertebrae have sophisticated the idea introduced by Gaf. A flexible posterior stabilization system, DYNESYS (dynamic neutralization system) developed in 1994 and now marketed by Zimmer (Warsaw, Ind.), is now gaining popularity among orthopedic surgeons in the US as an alternative to fusion. Anchored by pedicle screws, Dynesys uses preloaded stabilizing cords and spacers to provide uniform system rigidity. With the development of soft stabilization methods, fusion has become an outdated and inelegant technique that permanently eliminates normal biomechanical motion of the spine. The dynamic stabilization systems are important alternatives to fusion and are the future for the treatment of vertebral instability.

A need has thus arisen for improvements in dynamic stabilization instruments, and the present invention offers that advancement through the development of the flexible connecting rod for posterior implantation on damaged vertebrae.

In another application when a vertebra is broken, crushed or diseased, it is frequently necessary to ablate the body of the crushed or diseased vertebra. In order, however to prevent the spinal column from collapsing with damage to the spinal cord running in the vertebral foramen forward of the vertebral body, it is necessary to employ a spacer. This device is braced vertically between the bodies of the adjacent vertebrae and holds them apart at the desired spacing. A substitute vertebra with biofidelic properties would provide the optimum replacement Various implants have been developed to address structural failure of various parts of the spinal column. The prior art with respect to spinal column implants falls into two general categories: intervertebral disc prostheses, and rigid vertebral body prostheses.

Vertebral body prostheses have been disclosed in U.S. Pat. Nos. 3,426,364, 4,401,112, 4,554,914, 4,599,086, 4,932,975, and 5,571,192. The referenced patents typically are composed of a rigid, height adjustable device, typically a threaded cylinder or turnbuckle mechanism with anchoring plates. Another type of replacement device is composed of individual elements that are sized and adapted to be fitted together to provide support to the adjacent vertebra. This type of device has been described in U.S. Pat. Nos. 5,147,404 and 5,192,327.

The devices presented in the above patents are intended for situations where it is necessary to remove a vertebral body. That, in turn, requires the resection of adjacent intervertebral discs. A problem common to all of such prior devices however is that they adequately provide the structure of the removed vertebral body but fail to provide the flexibility of the removed intervertebral discs.

The rods disclosed herein provide a flexible implant that will flex, bend or curve to allow or duplicate the natural movement of the spinal segments.

These and other objects, features, advantages and aspects of the present invention will be better understood with reference to the following detailed description of the preferred embodiments when read in conjunction with the appended drawing figures.

SUMMARY OF THE INVENTION

The present invention overcomes the deficiencies and problems evident in the prior art as described herein above by combining the following features into an integral, longitudinally, laterally and torsionally flexible component.

A spine stabilization system for attachment to vertebral bodies to restore or maintain vertebral motion and provide support to the spinal column is disclosed. The system consists of a spinal element having a distal attachment end and a proximal attachment end. The center of the element, between the distal and proximal attachment ends has at least one flexible center section that has at least one slot of substantial length and width extending in a generally concentric path, or circumferential manner, following a serpentine or predetermined path generally around the tubular member. A serpentine path can be superimposed on the circumferential slot in the form of a generally sinusoidal wave. Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

Multiple slotted sections are separated by non-slotted areas. The slot can extend the entire length of the element or the proximal and distal attachment ends can be solid with the slotted section only being in the center. The slot has a width of about 1.0% to about 20% of the diameter of the spinal element. The element can be a tube having a hollow inside core forming an inner diameter and an exterior wall forming an exterior diameter having an inner diameter from about 10% to about 85% of the exterior diameter. Advantageously, the slot is cut at an angle normal to the shaft using a computer controlled cutting technique such as laser cutting, water jet cutting, milling or other means. Additionally, this slot can be cut at an angle to the normal, preferably from normal to about 45 degrees from the normal, so as to provide an undercut slot. In a preferred embodiment, the ratio of the amplitude of the serpentine path of the circumferential slot to the distance between slots is in the range from greater than 0.1 to about 0.8 and preferably in the range of about 0.04 to 0.06 for many applications. It will, however be evident to those skilled in the art that the preferred slot distance, as well as width of slot will depend on the end use, e.g. use on a large animal would require different dimensioning than use on a human To increase the flexibility of the component, a plurality of slots can be employed, relative to a shaft having a single slot of identical pattern. The serpentine, circumferential path forms a plurality of teeth and complimentary recesses on opposite sides of the slot. The slot has sufficient width to form an unbound joint that permits limited movement in any direction between the teeth and the recesses, thereby providing controlled flexibility in all directions upon application of tensile, compressive, and/or torsion forces. In a similar manner the slot can have increased width in one direction compared to another direction to provide increased flexibility in one direction. The flexible component can also have different degrees of flexibility along the length of the shaft. The varied flexibility can be achieved by having the width of the slot and/or the spacing of the circumferential slots vary along the length of the shaft. The varied flexibility corresponds to the spacing of the circumferential slot along the length of the shaft and/or the length of the section of the shaft having the circumferential slots. Alternatively, the width of the circumferential slot can vary along the length of the shaft to provide the varied flexibility. The rigidity of the flexible shaft can be achieved through the design of the slot pattern, thereby enabling the use of thinner walls than would otherwise be required to produce equivalent rigidity.

In some embodiments the slot can be filled, partially or entirely along the path of the slot, with a resilient material to control and vary rigidity. Further rigidity can be achieved by encapsulating the entire shaft thus forming an elastomer enclosed member. The resilient material can be an elastomer compound, such as urethane or a silicone compound, which can be of sufficient thickness to fill the slot and to encapsulate the entire shaft. The rigidity of the flexible shaft can be further achieved or varied through the use of filler material having different stiffness properties, thereby enabling the use of thinner walls than would otherwise be require to produce equivalent rigidity.

The element can have the elastomeric material in any or all of the following combinations: filling at least one of the at least one slot; at least a portion of the inside core; encompass at least a portion of the exterior diameter. Attachment members are used at the proximal and distal attachment ends to attach the element to the vertebral bodies. One or more central attachment members can be used to affix the element, in between the attachment ends, to vertebral bodies.

When the spinal element is used to replace one or more diseased or fractured vertebra, a preferred diameter is from about 0.5 to 1.0 inches. The attachment members at the proximal end and distal end are affixed to a superior and an inferior vertebra. The proximal and distal attachment ends have threaded receiving areas to receive attachment members. Preferably one of said threaded receiving areas is a right hand thread and the second a left hand thread. The attachment members can comprise a threaded end cap, a threaded rod threadably engage with the end cap, a ball end attached to the threaded rod, and an end plate dimensioned to rotatably receive the ball end on one surface and securing member receiving areas on a second surface. The securing member receiving areas can be nails affixed to the end plate or a plate surface that is conducive for bone ingrowth.

To stabilize a diseased or fractured vertebra to restore or maintain vertebral motion and provide support to the spinal column the distance between healthy superior vertebra and inferior vertebra adjacent to said diseased or fractured vertebra is determined. A flexible spinal element having a length to span the distance is selected and a first attachment member is attached to the superior vertebra and a second attachment member attached to the inferior vertebra. The spinal element is then attached to the first and second attachment members.

The disclosed system has several closely related embodiments, all using the flexible spinal element. The selection of a specific embodiment for a particular application will be obvious to one skilled in the medical arts upon reading the teachings herein.

It is a further object of this invention to provide a tubular device which will have certain axial, bending and torsional stiffness for a vertebral body replacement implant.

BRIEF DESCRIPTION OF THE DRAWINGS

These and other objects, features, advantages and aspects of the present invention will be better understood with reference to the following detailed description of the preferred embodiments when read in conjunction with the appended drawing figures.

FIG. 11 is a sectional illustration though the longitudinal axis, 8A-8A of the spinal element in FIG. 8 showing the resilient filler occupying the central core and filling the slot in accordance with the invention;

FIG. 12 is a magnified view of the area 111A of FIG. 11 in accordance with the invention;

DETAILED DESCRIPTION OF THE PREFERRED EMBODIMENTS

Definitions and Terms

Figure 1:
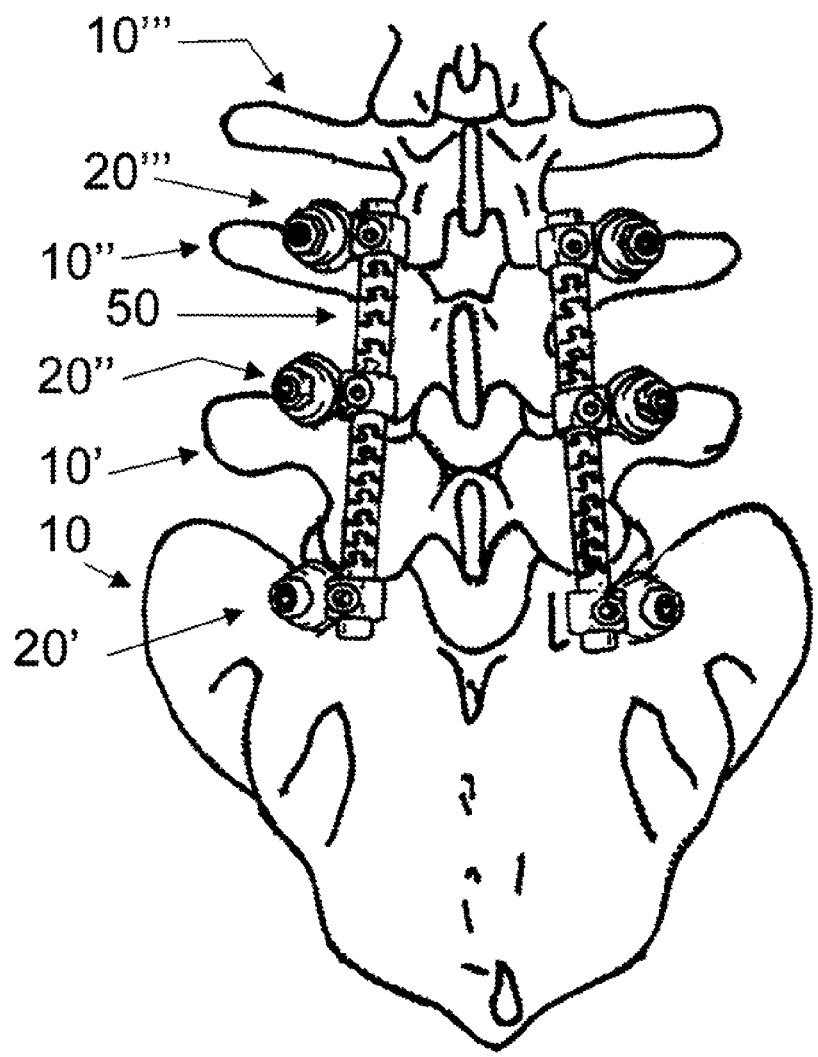
FIG. 1 is a schematic representation of a flexible spinal element attached to the lumbar region of the spine and having circumferential slots extending the majority of the length of the element in accordance with the invention.

The term slot as used herein, is defined in the American Heritage Dictionary, 3rd Edition, Copyright 1994, as follows:

For the purposes herein the terms "slit" and "slot" are used interchangeably, consistent with their definitions, as follows:

slot n. 1. A narrow opening; a groove or slit: a slot for coins in a vending machine; a mail slot.

2. A gap between a main and an auxiliary airfoil to provide space for airflow and facilitate the smooth passage of air over the wing.

For the purposes herein the term pitch as used herein is defined as:

pitch—n.1. The distance traveled by a machine screw in one revolution.

2. The distance between two corresponding points on adjacent screw threads or gear teeth.

For the purposes herein the term "cycle" shall refer to:

Cycle—1. An interval of time during which a characteristic, often regularly repeated event or sequence of events occurs: Sunspots increase and decrease in intensity in an 11-year cycle.

2.a. A single complete execution of a periodically repeated phenomenon: A year constitutes a cycle of the seasons.

2b. A periodically repeated sequence of events: cycle includes two halves of the sine-wave like undulation of the slot path.

For the purposes herein the term "amplitude" shall refer to the maximum absolute value of the periodically varying quantity of the slot.

For the purposes herein the term "frequency" shall refer to the number of times a specified phenomenon occurs within a specified interval:

Frequency.

1a. Number of repetitions of a complete sequence of values of a periodic function per unit variation of an independent variable.

1 b. Number of complete cycles of a periodic process occurring per unit time.

1c. Number of repetitions per unit time of a complete waveform, as of an electric current. The number of times the cycles form a repetitive pattern in one unit of length is the frequency of the slot pattern. The number of cycles "C" of the slot undulations superimposed upon the circumferential path which are present in one revolution around the shaft, is referred to as the cycles per revolution.

For the purposes herein the coined term "Biofidelic" shall refer to the mechanical structures that attempt to duplicates biological structures with a high accuracy of fidelity.

For the purposes herein the term "spinal element" shall refer to a solid rod or tube manufactured of a biocompatible material that can receive a slot or cut to provide flexibility.

For the purposes herein the term "dynamic stabilization systems" shall refer to spinal instrumentation devices that stabilizes the damaged spine while permitting motion.

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention. Accordingly, the descriptions that follow are to be understood as illustrative and exemplary of specific structures, aspects and features within the broad scope of the present invention and not as limiting of such broad scope.

The present invention is directed to dynamic stabilization systems for use with the anterior, antero-lateral, lateral, and/or posterior portions of at least one motion segment unit of the spine. The systems of the invention are designed to be conformable to the spinal anatomy and provide controlled, dynamic stabilization.

The system of the invention can be used on the cervical, thoracic, lumbar, and sacral segments of the spine. The size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with the disclosed spine stabilization system restores a more natural movement and provides added support to the strain-susceptible area.

One embodiment of the spine stabilization system of the present invention includes bone fasteners, for example pedicle screws, the disclosed end plates or hooks, and at least one of the disclosed flexible spinal elements, with or without additional connecting rods. The flexible element advantageously provides desirable properties for bending or twisting that allows the system to accommodate the natural spine movement. The flexible element preferably approximates or resembles a relatively circular metallic or polymeric tube or rod with an appropriately formed series of slots that extends circumferentially around the shaft, the basic concept of which is described by Krause et al (U.S. Pat. Nos. 6,053,922 and 6,447,518) and are incorporated herein as though recited in full. In another embodiment, the spinal element and flexible segments of the element can be combined with a polymeric material as described hereinafter.

In some embodiments the central portion of the flexible element is hollow, resembling a hollow tube. A skilled artisan would appreciate that there are several ways to form a hollow tube, regardless of whether it is circular or any other cross-sectional shape. For example, extruding a material, such as metal or polymeric materials, through a die, can form the tube with one or more of the patterns described hereinafter then be cut into the extruded material. For instance, a tube can have a slit or serpentine cut along at least a portion of the tube or the tube can have a plurality of slits cut into its surface, by using a laser or by other suitable methods.

The following examples describe embodiments using a solid rod or tube. It should be understood that in these examples the flexible elements described herein can be replaced with flexible elements having different shapes or configurations, including, but not limited to, the many variations described herein.

The invention relates to a flexible spine stabilization system having one or more flexible segments within a spinal element. The flexibility is created through the use of at least one circumferential slot formed in the spinal element. Additional flexible segments also have at least one circumferential slot. One or more fasteners are connected to or in communication with the distal and proximal attached ends of the spinal elements as known in the medical arts. In another embodiment the flexible spine stabilization system has a flexible segment that has at least one circumferential slot within a section of the spinal element that is embedded within a polymer or other flexible material so as to fill the slot with the flexible material. In an additional embodiment the flexible spine stabilization system uses a hollow flexible element that encompasses a polymer or other flexible material within its central core without extending into the circumferential slot(s). A further embodiment uses a flexible slotted segment within the spinal element that contains a polymer or other flexible material within the central core with the flexible material extending radially outward through the circumferential slot(s). The flexible spine stabilization system can further incorporate a flexible slotted segment that contains a polymer or other flexible material within the central core of the spinal element and/or flexible segment that extends radially outward through the slot and encompasses the outer surface of the spinal element and/or the flexible segment.

Another important aspect of this invention therefore lies in providing a prosthesis for total replacement of a vertebral body and adjacent discs that will provide the flexibility and stiffness of the resected vertebra and, when properly in place, provides a stress environment at the prosthesis/bone interface similar to normal in vivo conditions. Specifically, the invention can be utilized to produce an implant in which the normal ranges of movement are preserved, the prosthesis permitting limited longitudinal flexure, slight compression and expansion, and even a limited degree of torsional movement that at least approximates a normal vertebral response.

Figure 2:
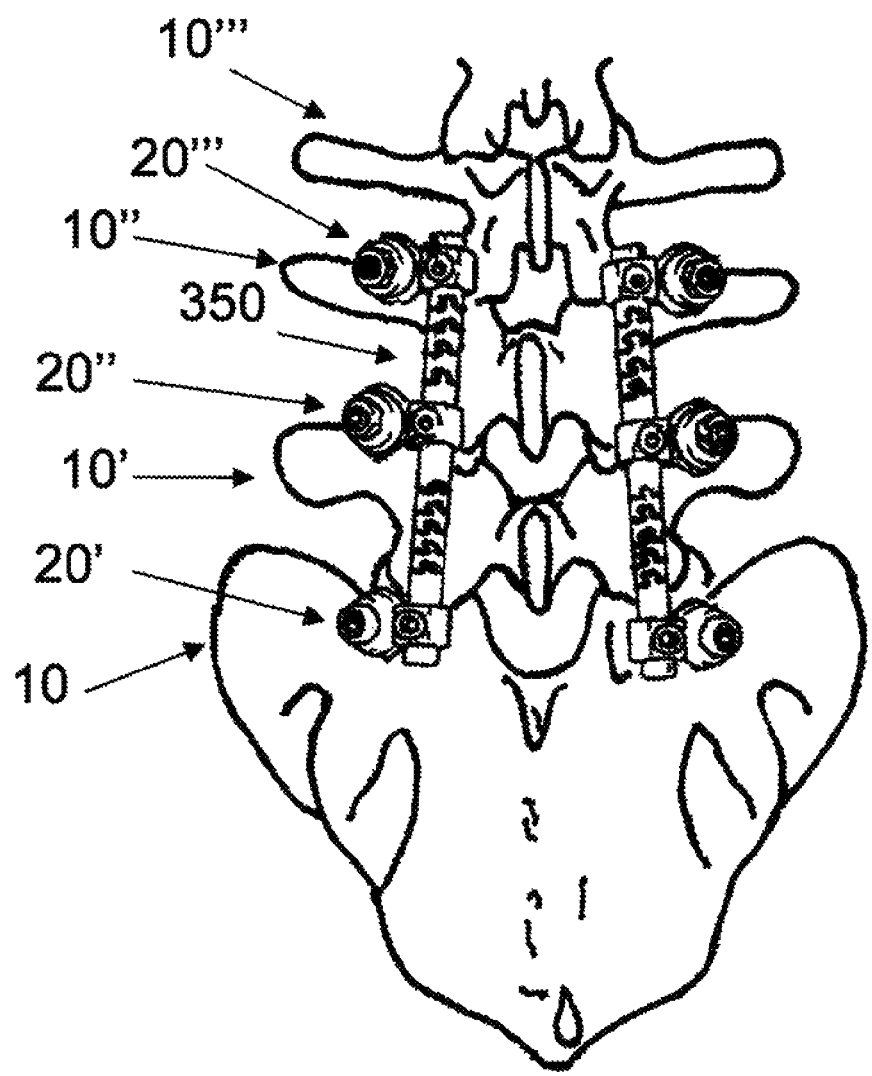
FIG. 2 is a schematic representation of a flexible spinal element attached to the lumbar region of the spine and having the circumferential slots extending only between the attachment members in accordance with the invention.
Figure 5:
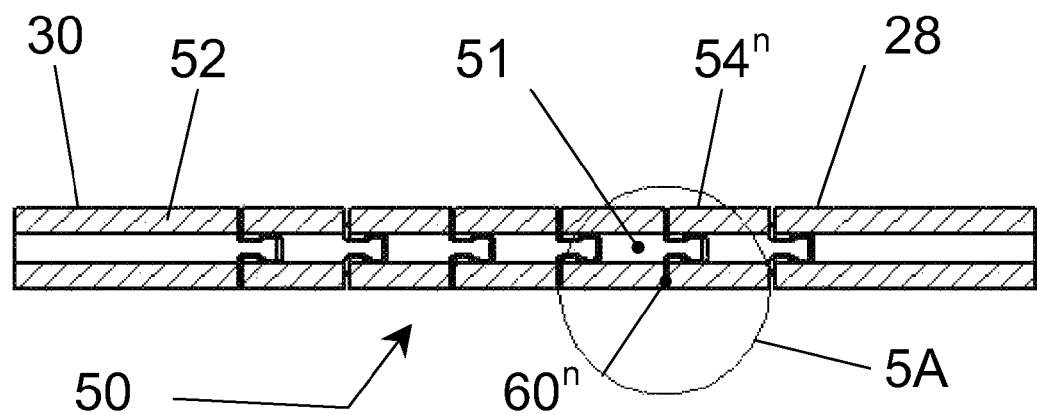
FIG. 5 is a cross sectional view of the flexible spinal rod through the longitudinal axis of FIG. 3, showing general pattern of the serpentine, circumferential slots along the length of the rod in accordance with the invention.

The dynamic stabilization system of the present invention generally consists of a spinal element 50 and pedicle screws 20, as illustrated in FIG. 1, which are connected to two or more vertebra 10, 10', 10" and 10''' spanning the area fused or damaged area. The spinal element 50 in this embodiment generally consists of a hollow tube having an outer surface 54 and a hollow central core 55 as illustrated in FIGS. 2 and 5 hereinafter. A slot 60 is cut through the wall 52 of the spinal element 50 to form a serpentine, circumferential path that extends around the entire, or partial, length of the spinal element 50. Multiple circumferential slots 60', 60" ... $60^n$ are situated continually at prescribed or varying intervals over all or most of the length of the spinal element 50 enabling the majority of the element 50 to flex. The number of slots "n" can vary dependent upon the flexibility desired. The flexibility will be dependent upon the spacing "C" as well as the amplitude "A" of the serpentine slot 60 and the solid section 54 between slots 60. Typically the ratio of the amplitude to the spacing (A/C) is between 0.1 and 0.9. Although pedicle screws 20 are illustrated herein as being attached to the proximal attachment end 28, the distal attachment end 30, as well as the central portion of the spinal element 50, hooks or other known attachment members can be substituted as known in the art. It should be noted that the pedicle screws can be affixed to slotted portions of the spinal element as well as the non-slotted portions.

Figure 3:
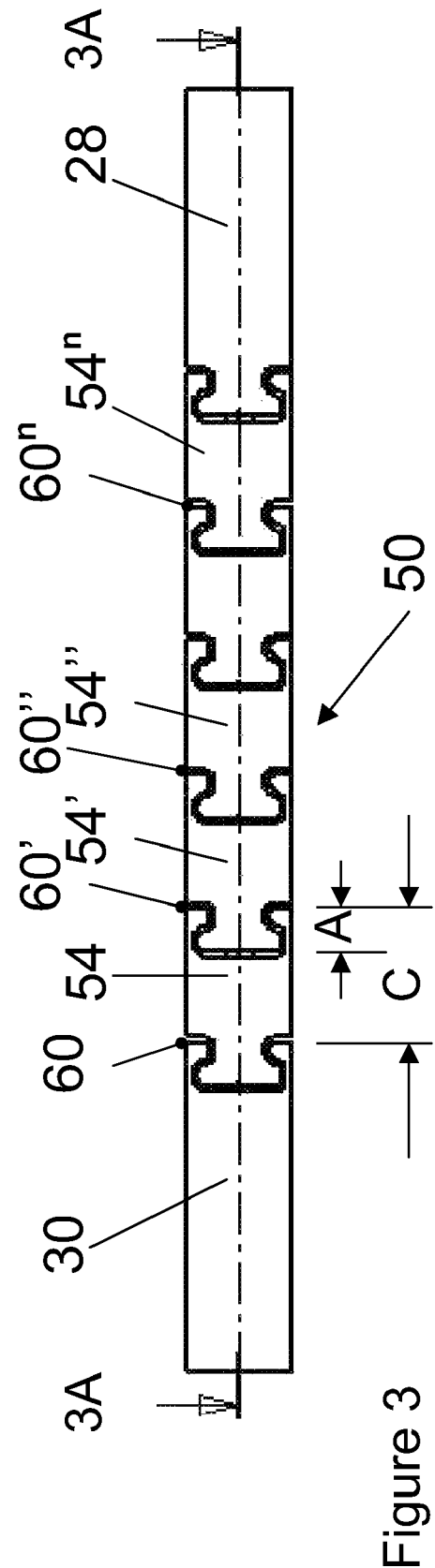
FIG. 3 is a schematic representation of the flexible spinal rod of FIG. 1, showing general pattern of the circumferential serpentine slots along the length of the rod in accordance with the invention.
Figure 4:
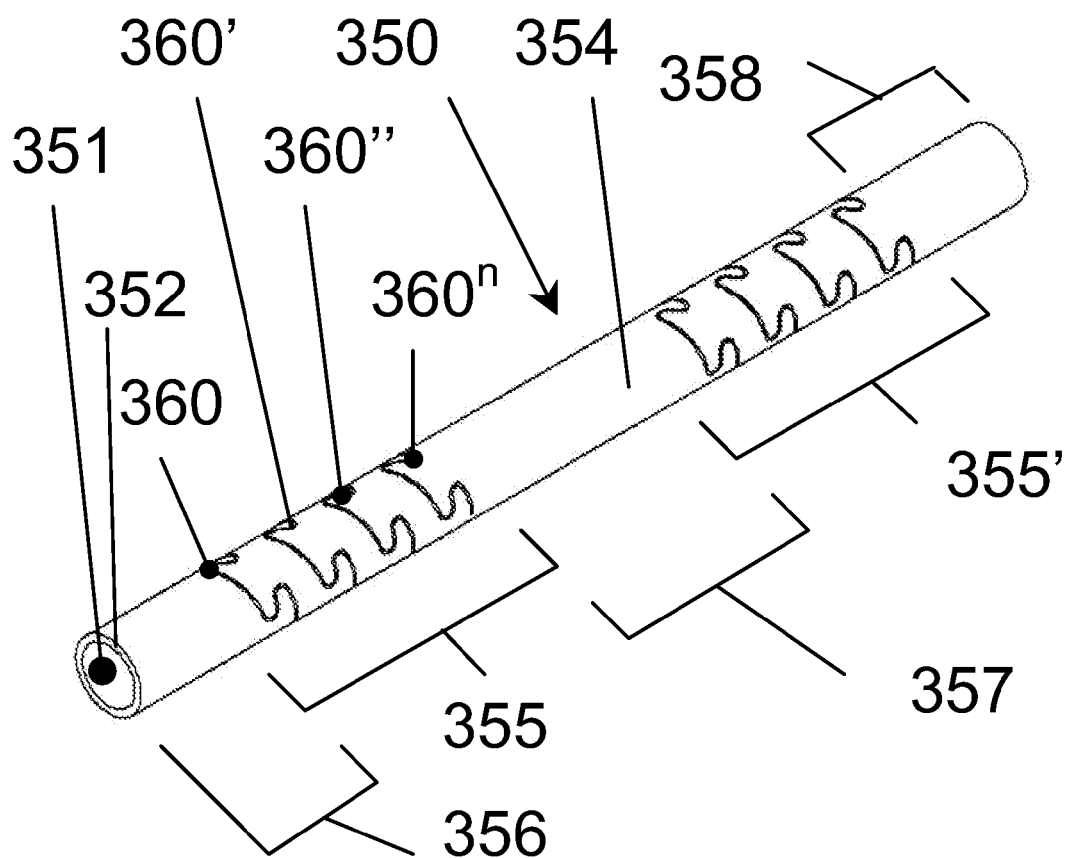
FIG. 4 is perspective view of spinal element of FIG. 2, showing the segmental segments containing the serpentine slots between attachment areas.

In FIG. 3, the dynamic stabilization system of the present invention generally consists of a spinal element 350 and pedicle screws 20 which are connected to two or more vertebra 10, 10', 10" and 10''' spanning the fused or damaged area. As with the embodiment of FIG. 1, the spinal element 350 generally consists of a hollow tube having an outer surface 354 and a hollow central core 351 as illustrated in FIG. 4. A slots 360, 360', 360", ... $360^n$ are cut through the wall 352 of section of the spinal element 350 to form a flexible segment 355. In this embodiment the slots 360 ... $360^n$ allow for flexibility only within the flexible segments 355 and 355'. The sections of the spinal element 350 that are not slotted remain relatively rigid and are used for attachment with the pedicle screws 320 at the proximal attachment end 356 distal attachment end 358 and/or central section 357. Although FIGS. 3 and 4 illustrate two flexible sections 355 and 355', the number of flexible sections would be dictated by the number of vertebral discs requiring flexible support and would be obvious to those skilled in the art.

Figure 6:
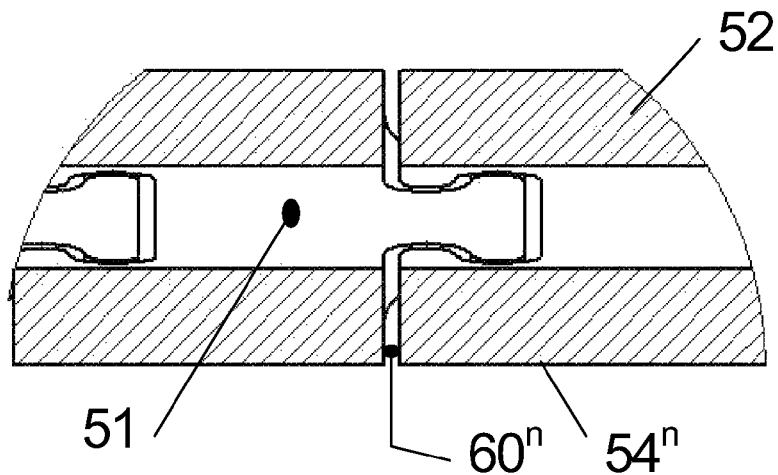
FIG. 6 is an exploded view of section 5A showing the gap and interlocking of the serpentine slot.

The sectional view 3A-3A of spinal element 50 of FIG. 2 is shown in FIG. 5. A magnified view 5A of the slot 60 is illustrated in FIG. 6. The slot 60 is representative of all the slots disclosed herein in that way that it is cut through the wall 52 into the core 51. Although the slots disclosed herein are of different patterns, this is purely a function of flexibility and all have the same basic construction. The criticality to the disclosed invention lies in the ratios and dimensions rather than the process of placing a rod or tube. In the following description of the criteria of the slots, no reference numbers specific to other figures are used, as the criteria are applicable to all slot configurations.

In order to provide the desired flexibility, while maintaining support, the width of the slot should not exceed about 0.075 of an inch in a rod having a diameter in the range from about 0.10 to about 1.0 inches, with a general width of about 0.005 to about 0.025 inches. Or alternatively stated, the slot width is between about 2.5% and about 20% of the diameter of the spinal element. The slot width typically determines the flexibility of the element; a larger slot width produces a more flexible element then an element with a smaller slot width.

Figure 7A:
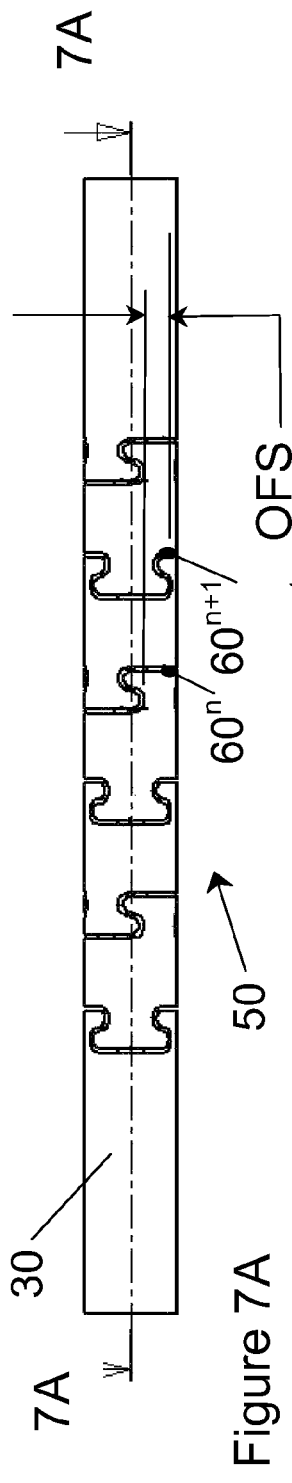
FIG. 7A is an illustration of variation of the change in orientation of the serpentine slot relative to the adjacent slot whereby the teeth of each adjacent circumferential slot is staggered or offset a variable distance.
Figure 7B:
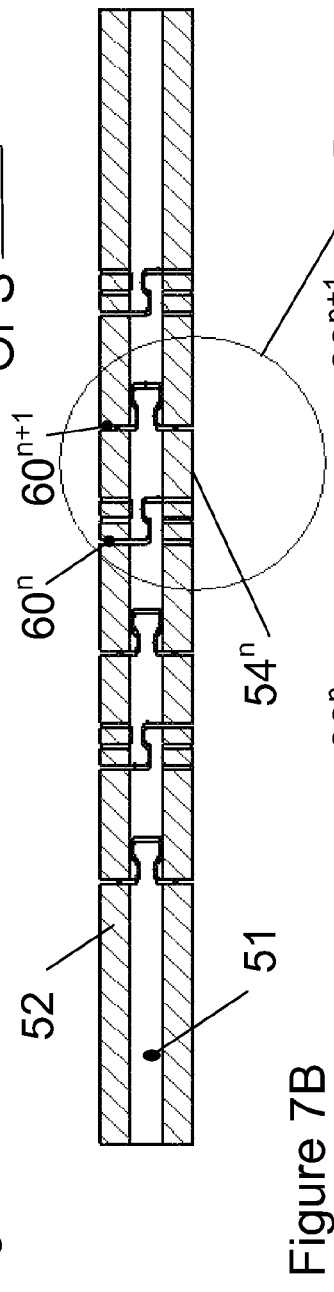
FIG. 7B is a cross sectional view of the flexible spinal rod through the longitudinal axis of FIG. 7A, showing general pattern of the offset serpentine, circumferential slots along the length of the rod in accordance with the invention.
Figure 7C:
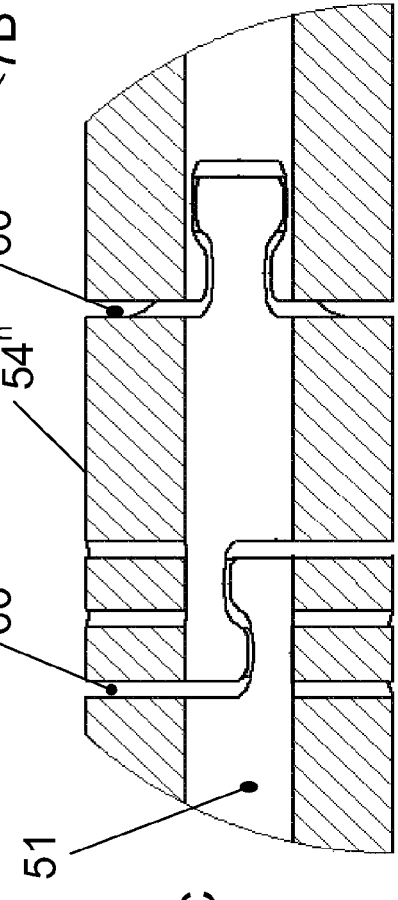
FIG. 7C is an exploded view of section 7B showing the gap and interlocking of the serpentine slot of two slots that have been offset or staggered.

In the embodiment illustrated in FIGS. 7A, 7B, and 7C, the serpentine pattern of slot $60^{n+1}$ is offset or staggered a rotational distance OFS from the adjacent slot $60^n$. By staggering the serpentine pattern as illustrated, the bending characteristics, i.e. the bending strength and flexibility, can be changed to provide differences or uniformity with respect to the rotational axis.

Figure 8:
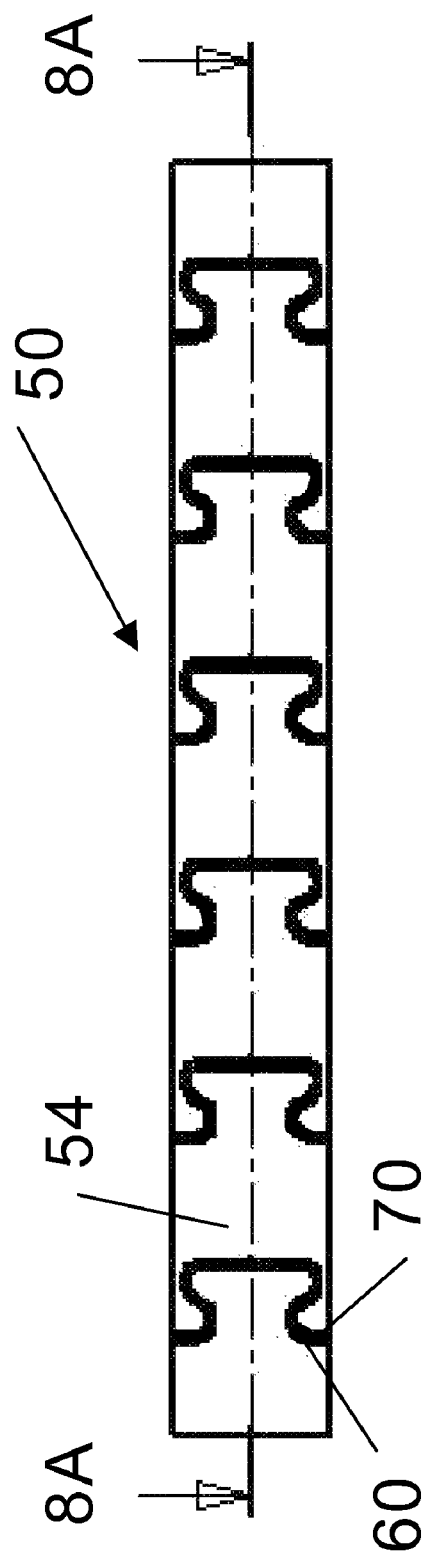
FIG. 8 is a schematic representation of the flexible spinal rod of FIG. 1, showing general pattern of the circumferential serpentine slots with an elastomer filler material in the slot.
Figure 9:
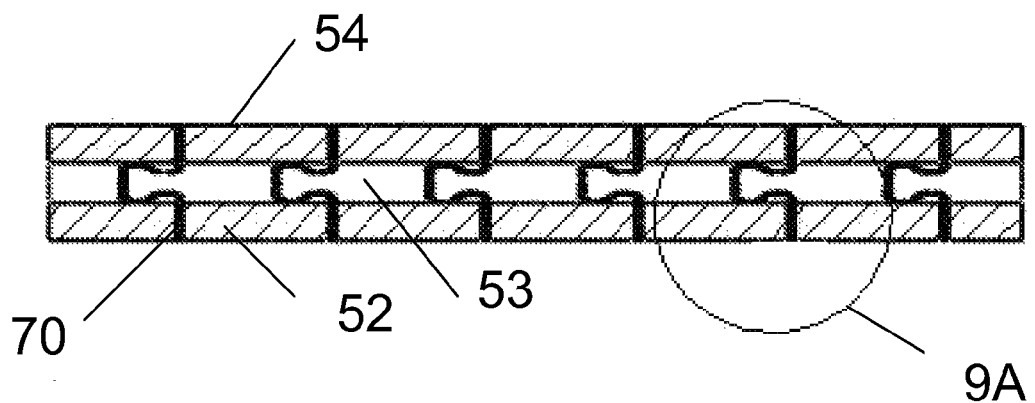
FIG. 9 is a sectional illustration though the longitudinal axis 8A-8A shown in FIG. 8 of the spinal element showing the slot with a resilient filler in a portion of the slot in accordance with the invention.
Figure 10:
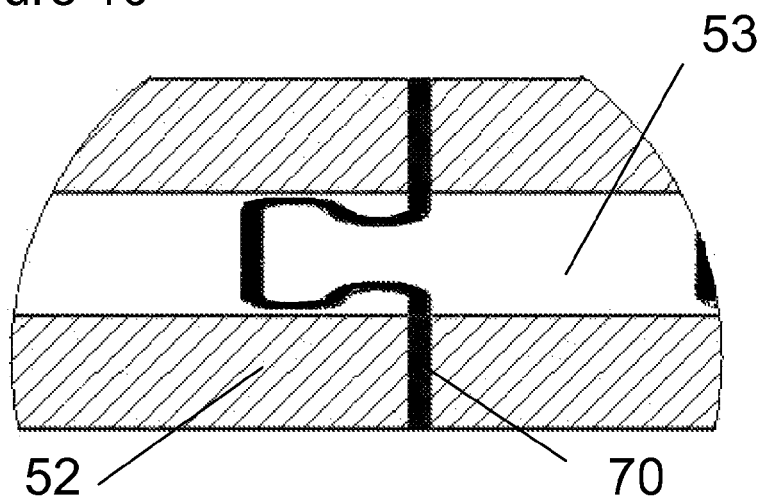
FIG. 10 is a magnified view of the area 9A in FIG. 9 in accordance with the invention.

In the embodiment illustrated in FIGS. 8, 9 and 10, a biocompatible resilient flexible or elastomeric material 70 fills only the slot 60 of the spinal element 50. The exterior surface 54 of the spinal element 50 remains uncovered by the material 70 as does the interior surface 53. The addition of the elastomeric material 70 to the slot 60 provides resistance to the flexibility of the spinal element 50 as well as preventing tissue and scar ingrowth into the slot. It should also be noted that the elastomeric material does not necessarily have to fill all slots in the rod, with the placement of filled and unfilled slots affecting the flexibility.

In FIGS. 11 and 12 the elastomeric material 170 completely fills the central core 155 and the slot 160 but does not cover the outer surface 154 of the element 150. The elastomeric material 170 can fill the only central core 155 adjacent to the slot or slots 160, or alternatively the entire central core 155. By filling the central core 155, flexibility is further decreased. By adjusting the amount of the central core 155 that is filled, the flexibility can be adjusted. Section 111A is illustrated in FIG. 12 in greater detail.

Figure 13:
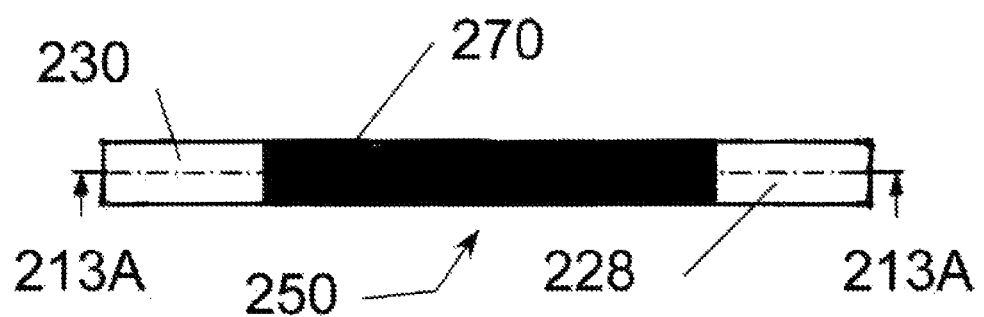
FIG. 13 is an exterior view of the spinal element with the center portion encapsulated with a resilient filler.
Figure 14:
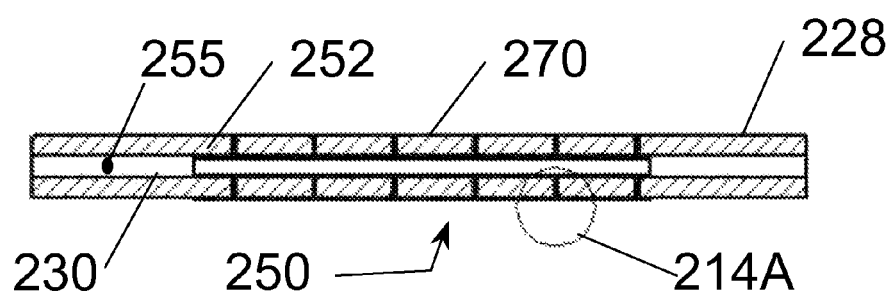
FIG. 14 is a sectional illustration though the longitudinal axis 213A of the spinal element in FIG. 13 showing the filled slot with a resilient filler encapsulating the entire tube but not filling the central core.
Figure 15:
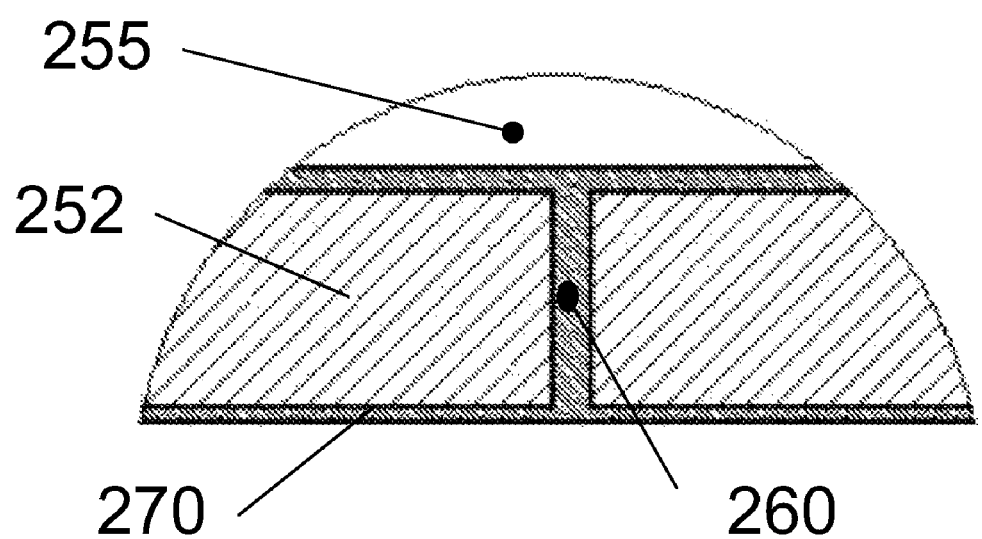
FIG. 15 is a magnified view of the area 214A in FIG. 14 in accordance with the invention.

In FIGS. 13, 14 and 15 the elastomeric material 270 encapsulates the spinal rod 250 as well as filling the slots 260. In this embodiment, the interior surface 230 and exterior surface 228 are covered with the elastomeric material 270 and the slots 260 are filled to prevent tissue ingrowth into the slots 260 and increase the stiffness of the spinal element. The core 255, of the spinal element 250, however, remains hollow as seen in section 213A-213A in FIG. 14. Although in these figures the elastomeric material 270 also fills the slots 260 passing through wall 252 as shown in FIG. 15 of the enlarged section 214A, it should be noted that the elastomeric material 270 can alternatively only encapsulate the spinal element 250 without filling the slots 260. Additionally, just the interior or exterior of the spinal element can be covered with the elastomeric material with the slots being either filled or unfilled. The encapsulation can be only at the portion of the rod that is flexible or can extend the entire length of the rod. As noted above, the addition of the elastomeric material 270 increases the resistance to flexing and is not reflective of the advantages of encapsulating the spinal element 250 with the elastomeric material 270.

Figure 16:
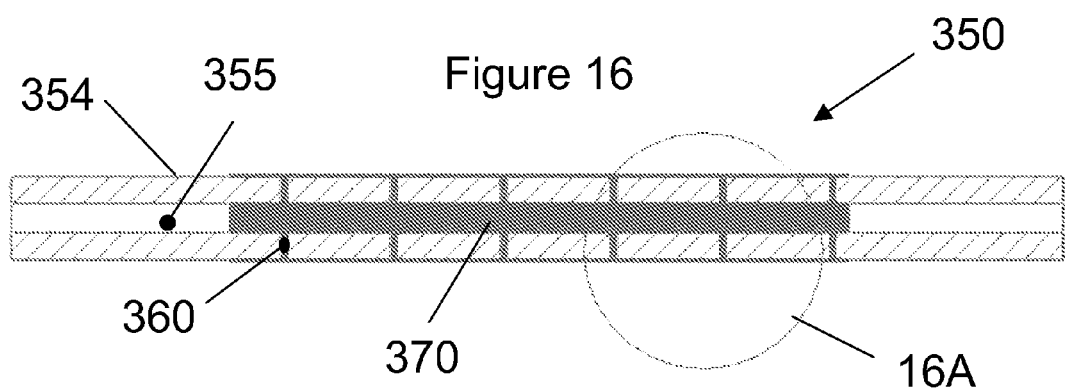
FIG. 16 is a sectional illustration though the longitudinal axis of the spinal element showing the resilient filler occupying the central core and encapsulating the entire tube in accordance with the invention.
Figure 17:
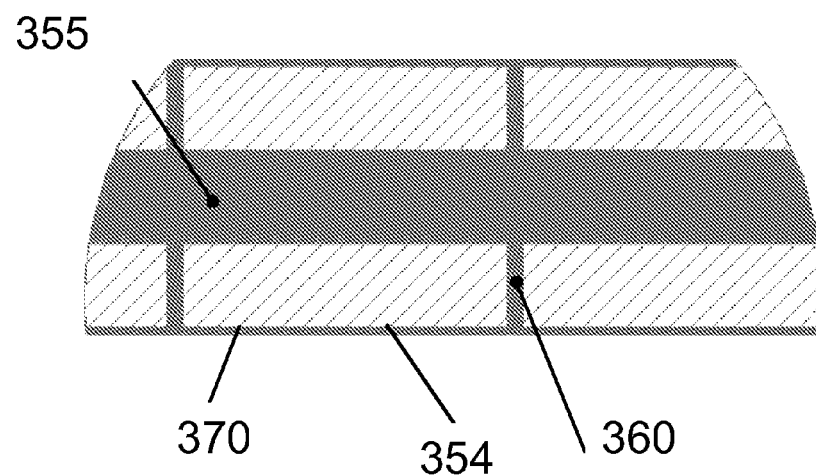
FIG. 17 is a magnified view of the area 16A of FIG. 16 in accordance with the invention.
Figure 18A:
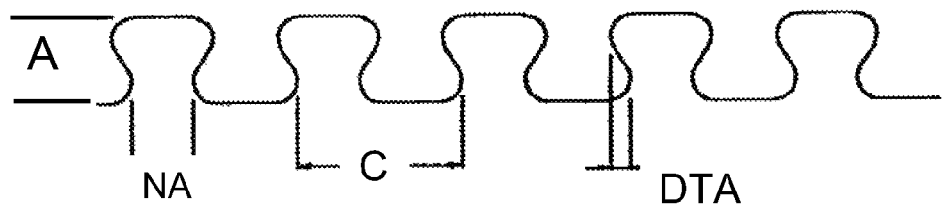
FIGS. 18a-18f show schematic representations of additional spiral slit patterns in accordance with the invention.
Figure 18B:
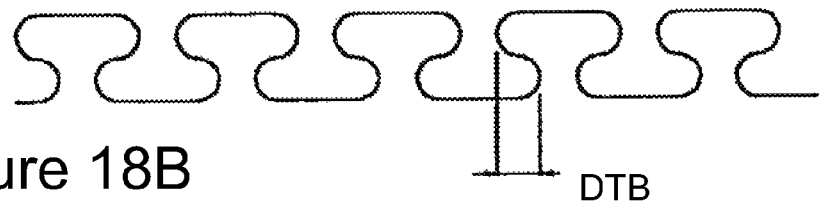
Figure 18C:
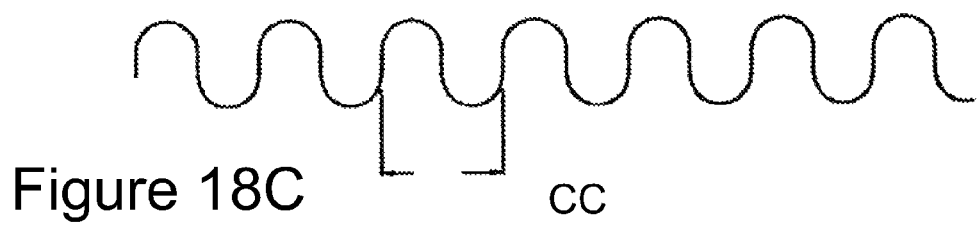
Figure 18D:
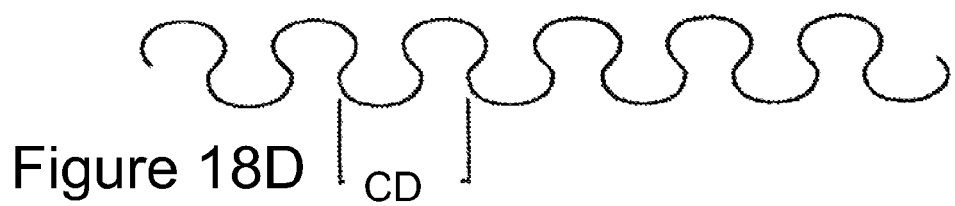
Figure 18E:
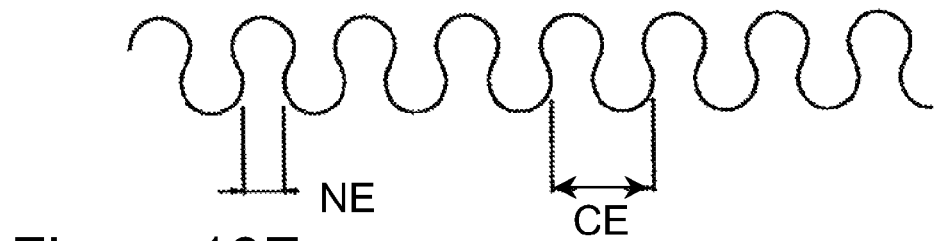
Figure 18F:

In FIGS. 16 and 17, the elastomeric material 370 fills the central core 355, slot 360 and covers the outer surface 354. As stated with reference to FIGS. 13 and 14, the elastomeric material as illustrated in all Figures herein can either fill the central core adjacent to the slots or the entire length. This embodiment provides the greatest resistance to flexing when using the hollow tube.

It should be noted that the elastomeric material used herein can also be varied in its material properties, thereby further controlling the amount of flexibility.

A variety of slot patterns are illustrated in FIG. 18 A-F. The patterns are representative of patterns which can be used and are not intended to be all inclusive. As illustrated in FIG. 18A, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 18A and DTB for FIG. 18B. The pattern of 18C, does not provide dovetailing, and requires full encapsulation for structural integrity. Additional patterns, as shown in FIGS. 18D, 18E, and 18F can have a configuration as illustrated in U.S. Pat. No. 6,447,518, the disclosure of which is incorporated herein by reference, as though recited in detail.

Figure 19:
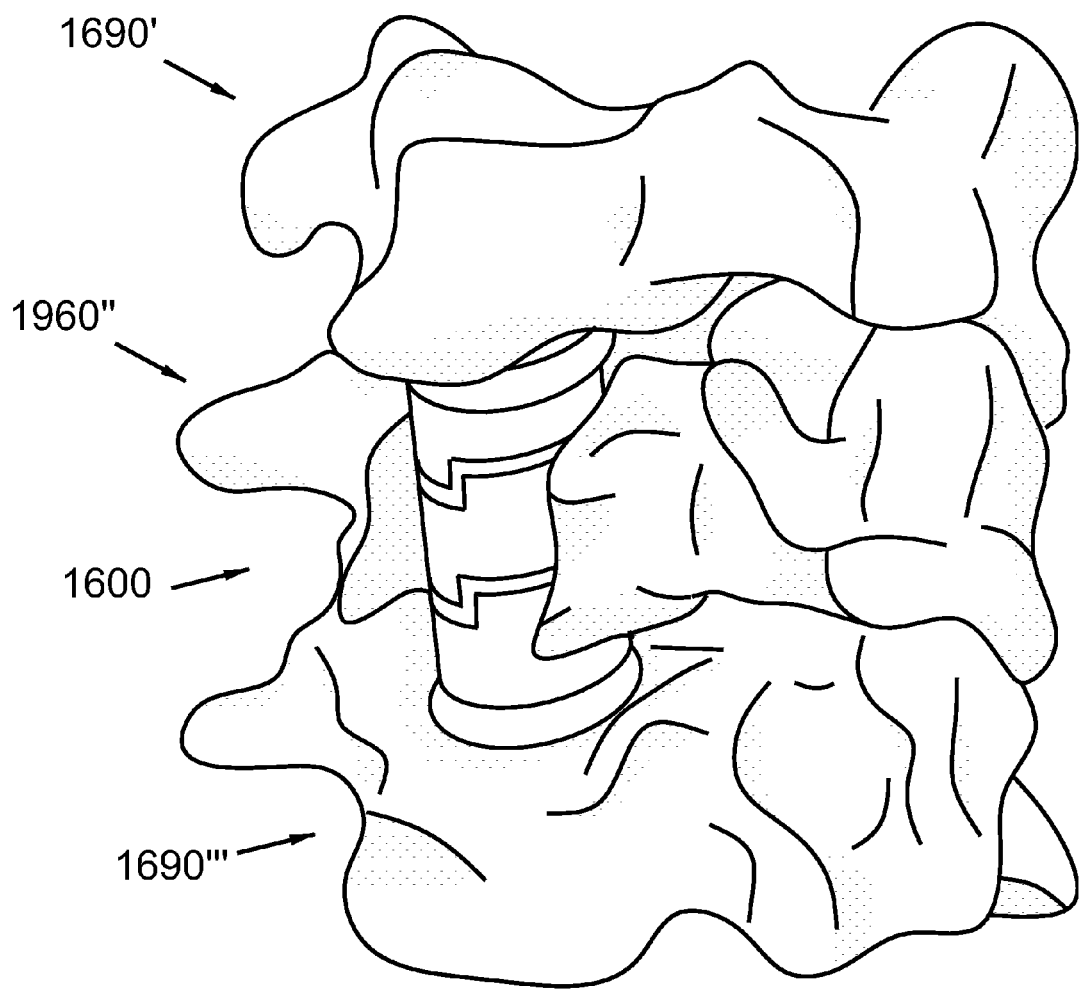
FIG. 19 is schematic representation of one embodiment of the spinal element as a vertebral replacement inserted between vertebra of the spine in accordance with the invention.
Figure 20:
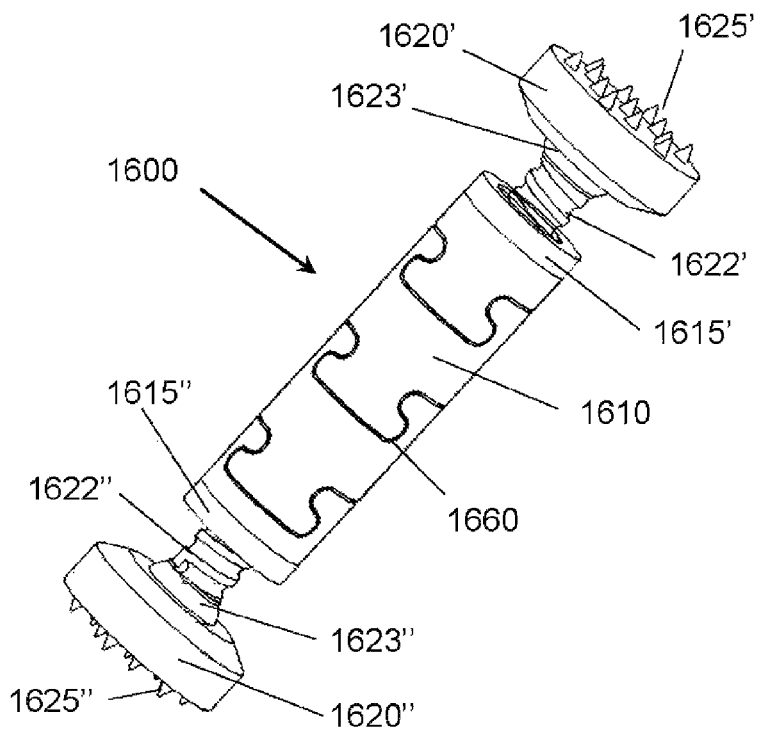
FIG. 20 is an illustration of the disclosed vertebral body replacement consisting of a central flexible core with and the previously described serpentine circumferential slots and adjustable height end caps for securing the device to the adjacent vertebra in accordance with the invention.
Figure 21:
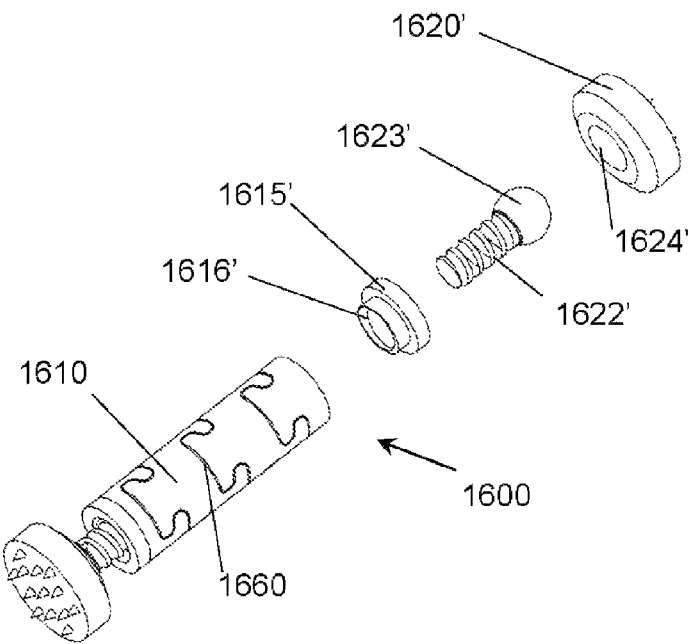
FIG. 21 is an exploded view of the vertebral body replacement in accordance with the invention.

In another embodiment of the invention illustrated in FIGS. 19-21, the spinal element disclosed heretofore is used as a central section of a vertebral body replacement implant 1600. As with the embodiments disclosed heretofore, the flexible portion of the implant is formed of rigid biocompatible material such as, for example, stainless steel or titanium. Through the addition of the endplates 1620' and 1620", the disclosed implant can be used the cavity left after removal of a diseased or defective vertebra 1690" in a human or animal spine. The vertebral body replacement 1600 is situated spanning the diseased vertebra 1690" and attached to the adjacent vertebra 1690' and 1690'''.

The spinal element 1610, as shown in FIGS. 20 and 21, is connected to an upper endplate 1620' and lower endplate 1620" by means of a threaded rods 1622' and 1622" respectively. The threaded rod 1622' and 1622" are movably secured to end caps 1615' 1615" respectively through internal treads 1616' and 1616" in the endcaps 1615' and 1615" to allow for height adjustment. The end caps 1615' and 1615" can be affixed to the spinal element 1620 during manufacture or by other means known in the medical arts. Preferably one endplate 1620' has right handed thread and the opposite endplate 1620" has a left handed thread such that rotating the spinal element 1610 will cause an increase in the overall distance between the endplates 1620' and 1620" from the spinal element 1610 and rotation in the opposite direction will reduce the overall distance. The balls 1623' and 1623" at the ends of the threaded rods 1622' and 1622" are attached to the endplates 1622' 1622" through sockets 1624' and 1624" or similar rotational allowance coupling to allow for angular alignment to the vertebra, one end of which is illustrated in an exploded view in FIG. 20. Attachment to the upper endplate 1620' and the lower endplate 1620" to the adjacent vertebra 1510' and 1510" is through spikes 1625' and 1625" respectively, or other means known in the medical arts. The spinal element 1610, FIGS. 20 and 21, has a circumferential, serpentine slot 1660 machined in the body. The slot 1660 configuration and properties of the cylindrical body and optional elastomeric filler are designed to duplicate the stiffness, within a reasonable allowance, of the vertebra and adjacent intervertebral disc of human specimens. The slot 1660 cut into the spinal element 1610 can have an elastomer (not shown) or otherwise flexible material interposed within the slot 1660 and/or the central core of the spinal element, as describe previously, to further enhance the flexibility of the shaft and to alter the torsional response or bending stiffness of the member. The elastomer can additionally be used as a shock absorbing or cushioning member. To facilitate manufacture, and to provide protection of the tubular member, the elastomer can encapsulate the entire shaft or coupler, thus forming a tubular construction. Alternatively, the interior of the spinal element 1610 can be threaded fully or partially and the threaded rods 1622' 1622" affixed directly to the spinal element 1610 thereby eliminating the endcaps 1615' 1615".

The upper and lower endplates 1620' 1620" are configured to provide anchoring with the adjacent vertebra by means of spikes 1625', 1625" (illustrated), screws or other means. The end plates can contain holes through which the screws or pins can be passed into the adjacent vertebra. The screws or fixation pins would pass through the implant endplate and/or alignment disc to rigidly fix the implant to the adjacent vertebra and allow for the natural curvature of the spine. It the thickness of the endplates will preferably be supplied in various thicknesses to compensate for the height of the removed vertebra and discs.

The method of implantation of the spinal element as configured as a vertebral body replacement implant 1600 of a diseased or fracture vertebra 1690 to restore the height and functionality of the spinal column is described. The assembled endplates 1620' 1620" and threaded rod 1622' 1622" as shown in FIG. 21 are affixed into the appropriate sized spinal element 1610 with endcaps 1615' 1615" previously attached. The endcaps 1615' 1615" can be affixed to the spinal element 1610 at the time of manufacture or subsequently as known in the medical arts. The spinal element 1610 and endplates 1620' 1620" are dimensioned to allow for minimum or appropriate height, upon addition of the endplates 1620' and 1620" to be inserted in the prepared cavity of the vertebra 1690. The spinal element 1610 is rotated to expand the implant 1600 to engage the upper endplate 1620' and the lower endplate 1620" to the adjacent vertebra 1510' and 1510" through spikes 1625', 1625" or other means known in the medical arts.

It is to be understood that surface of the endplate interfacing with the vertebra can be harmonious to facilitate and promote bone ingrowth. As well known in the art, sintered metal surfaces and other porous materials have been found particularly effective for that purpose. While a detailed discussion is believed unnecessary, it will be appreciated that the attachment screws are particularly important for initial fixation and for immobilizing the implant with respect to the adjoining vertebrae so that bone ingrowth may ultimately occur, at which time the ingrowth becomes a major factor in maintaining fixation. Another major factor in achieving and maintaining fixation is the limited yieldability of the prosthesis that, by mimicking the action of the replaced components, reduces the stresses at the bone/prosthesis interfaces.

While the foregoing has disclosed embodiments of the invention in considerable detail, it will understood by those skilled in the art that many of these details may be varied without departing from the spirit and scope of the invention.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A spine stabilization system for attachment to vertebral bodies to restore or maintain vertebral motion and provide support to the spinal column comprising an elongated spinal element having:
   (i) a distal attachment end;
   (ii) a proximal attachment end; and
   (iii) at least one flexible center section, said center section being positioned between said distal end and said proximal end, each of said at least one flexible center section having at least two spaced slots, each of said at least two spaced slots extending circumferentially around said spinal element following a serpentine path, said serpentine path forming a plurality of interlocking teeth.

2. The spinal stabilization system of claim 1 wherein said spinal element is a tube, said tube having a hollow inside core forming an inner diameter and an exterior wall forming an exterior diameter.

3. The spinal stabilization system of claim 2 further comprising an elastomeric material filling at least one of said at least one slot.

4. The spinal stabilization system of claim 2 further comprising an elastomeric material filling within at least one portion of said inside core adjacent to said at least one flexible center section.

5. The spinal stabilization system of claim 4 wherein said elastomeric material filling said insider core extends through, and fills, said at least two spaced circumferential slots.

6. The spinal stabilization system of claim 5 wherein said elastomeric material encompasses at least a portion of said exterior diameter of said spinal element.

7. The spinal stabilization system of claim 4 wherein said elastomeric material encompasses at least a portion of said exterior diameter of said spinal element.

8. The spinal stabilization system of claim 2 wherein said elastomeric material encompasses at least a portion of said exterior diameter of said spinal element.

9. The spinal stabilization system of claim 8 wherein said elastomeric material encompassing said exterior diameter extends through, and fills, said at least two spaced circumferential slots.

10. The spinal stabilization system of claim 2 wherein said inner diameter ranges from about 10% to about 85% of said exterior diameter.

11. The spinal stabilization system of claim 1 further comprising at least two attachment members, said at least two attachment members affixing said proximal attachment end and said distal attachment end to said vertebral bodies.

12. The spinal stabilization system of claim 1 further comprising at least one central attachment member, said at least one central attachment member being positioned between said proximal attachment end and said distal attachment end to attach said spinal element to vertebral bodies.

13. The spinal stabilization system of claim 1 wherein a first of said at least one flexible center section and a second of said at least one flexible center section is separated by a non-slotted section.

14. The spinal stabilization of claim 1 wherein said proximal attachment end and said distal attachment end are non-slotted.

15. The spinal stabilization system of claim 14 wherein a first of said at least one flexible center section and a second of said at least one flexible center section is separated by a non-slotted section.

16. The spinal stabilization system of claim 1 wherein said at least two spaced circumferential slots have a width of about 1.0% to 20% of the diameter of said spinal element.

17. A spine stabilization system for attachment to vertebral bodies to restore or maintain vertebral motion and provide support to the spinal column comprising an elongated spinal element being:
   a. a tube, said tube having a hollow inside core forming an inner diameter and an exterior wall forming an exterior diameter, said inner diameter ranging from about 10% to about 85% of said exterior diameter, said tube having
      i. a distal attachment end;
      ii. a proximal attachment end; and
      iii. at least one flexible center section, said center section being positioned between said distal end and said proximal end, each of said at least one flexible center section having at least two spaced circumferential slots extending around said center section following a serpentine path, said serpentine path forming a plurality of interlocking teeth around each of said at least one flexible center section, said at least two spaced circumferential slots having a width of about 1.0% to 20% of the diameter of said exterior diameter,
   b. at least two attachment members, said at least two attachment members affixing at least said proximal attachment end and said distal attachment end.

18. The spinal stabilization system of claim 17 further comprising an elastomeric material at least one location from the group of filling said at least two spaced circumferential slots, filling at least a portion of said central core, encompassing at least a portion of said spinal element.

19. The spinal stabilization system of claim 17 wherein said spinal element is a cylinder having a diameter ranging from about 0.5 to 1.0 inches for replacing one or more diseased or fractured vertebra.

20. The spinal stabilization system of claim 19 wherein said spinal element at said proximal attachment end and said distal attachment end have attachment members for attachment to a superior vertebra and inferior vertebra.

21. The spinal stabilization system of claim 20 wherein each of said attachment members, comprise:
   a. a threaded end cap,
   b. a threaded rod, said threaded rod being dimensioned to threadably engage with said end cap c. a ball end, said ball end being attached to said threaded rod,
d. an end plate, said end plate being dimensioned to rotatably receive said ball end, and having securing member receiving areas.

22. The spinal stabilization system of claim 21 wherein a first of said threaded end cap has a right hand thread and a second of said threaded end cap has a left hand thread.

23. The spinal stabilization system of claim 21 wherein said securing member receiving areas are nails affixed to said end plate.

24. The spinal stabilization system of claim 21 further comprising an elastomeric material at least one location from the group of filling said at least one slot, filling at least a portion of said central core, encompassing at least a portion of said spinal element.

25. The spinal stabilization system of claim 21 wherein said end plate surface is conducive for bone ingrowth.

26. The spinal stabilization system of claim 17 wherein said spinal element at said proximal attachment end and said distal attachment end have threaded receiving areas to receive said attachment members, one of said threaded receiving areas being a right hand thread and a second of said threaded receiving areas being a left hand thread.

27. A method of stabilizing diseased or fractured vertebra to restore or maintain vertebral motion and provide support to the spinal column comprising the steps of:
a. determining the distance between healthy superior vertebra and inferior vertebra adjacent to said diseased or fractured vertebra
b. selecting a flexible spinal element to span said distance, said flexible spinal element having a distal attachment end, a proximal attachment end and at least one flexible center section, said center section being positioned between said distal end and said proximal end, each of said at least one flexible center section having at least two spaced slots, each of said at least two spaced slots extending circumferentially around said spinal element following a serpentine path, said serpentine path forming a plurality of interlocking teeth,
c. attaching a first attachment member to said superior vertebra and a second attachment member to said inferior vertebra
attaching said spinal element to said first attachment member and said second attachment members.

\* \* \* \* \*